(12) United States Patent
Gavin et al.

(10) Patent No.: US 8,870,811 B2
(45) Date of Patent: Oct. 28, 2014

(54) PERITONEAL DIALYSIS SYSTEMS AND RELATED METHODS

(75) Inventors: David A. Gavin, Clayton, CA (US); Thomas I. Folden, Alamo, CA (US)

(73) Assignee: Fresenius Medical Care Holdings, Inc., Waltham, MA (US)

(*) Notice: Subject to any disclaimer, the term of this patent is extended or adjusted under 35 U.S.C. 154(b) by 2342 days.

(21) Appl. No.: 11/513,629

(22) Filed: Aug. 31, 2006

(65) Prior Publication Data

US 2008/0125693 A1 May 29, 2008

(51) Int. Cl.
*A61M 1/00* (2006.01)
*A61M 1/28* (2006.01)

(52) U.S. Cl.
CPC ............... *A61M 1/28* (2013.01); *A61M 1/288* (2013.01); *A61M 1/281* (2013.01); *A61M 1/287* (2013.01); *A61M 2205/12* (2013.01)
USPC ............................................. 604/29; 604/131

(58) Field of Classification Search
USPC .................................. 604/29, 131, 890.1, 500
See application file for complete search history.

(56) References Cited

U.S. PATENT DOCUMENTS

| | | |
|---|---|---|
| 1,406,372 A | 2/1922 | Grapp |
| 1,689,432 A | 10/1928 | Hartwig |
| 2,107,173 A | 2/1938 | Bauer |
| 3,130,289 A | 4/1964 | Katzman et al. |
| 3,605,783 A | 9/1971 | Pecker et al. |
| 3,694,625 A | 9/1972 | Cole |
| 3,808,401 A | 4/1974 | Wright et al. |
| 4,136,708 A | 1/1979 | Cosentino et al. |
| 4,489,535 A * | 12/1984 | Veltman ................. 53/431 |
| 4,508,622 A | 4/1985 | Polaschegg et al. |
| 4,676,467 A | 6/1987 | Palsulich |
| 4,778,451 A | 10/1988 | Kamen |
| 4,808,161 A | 2/1989 | Kamen |
| 4,826,482 A | 5/1989 | Kamen |
| 4,869,286 A | 9/1989 | Williams et al. |
| 4,902,282 A | 2/1990 | Bellotti et al. |
| 4,902,877 A | 2/1990 | Grasso et al. |
| 4,950,134 A | 8/1990 | Bailey et al. |
| 4,976,162 A | 12/1990 | Kamen |
| 5,002,471 A | 3/1991 | Perlov |
| 5,024,756 A | 6/1991 | Sternby |
| 5,088,515 A | 2/1992 | Kamen |

(Continued)

FOREIGN PATENT DOCUMENTS

| | | |
|---|---|---|
| EP | 0311848 | 4/1989 |
| EP | 1277485 | 11/2006 |

(Continued)

OTHER PUBLICATIONS

Translation of Sagatovich by Irina Knizhnik, USPTO Translations branch Sep. 25, 2008.*
Impact of sodium and ultrafiltration profiling on haemodialysis-related hypotension, NDT Advance Access published online on Sep. 5, 2006, Yi Lun Zhou, Hui Lan Liu, Xiao Feng Duan, Ying Yao, Yi Sun, and Qun Liu.

(Continued)

*Primary Examiner* — Kevin C Sirmons
*Assistant Examiner* — Phillip Gray
(74) *Attorney, Agent, or Firm* — Fish & Richardson P.C.

(57) ABSTRACT

Peritoneal dialysis systems and related methods are disclosed. The methods can include combining a first solution having a first concentration of a solute with a second solution having a second concentration of the solute to form a custom dialysate, e.g., according to a specific prescription for a patient.

41 Claims, 7 Drawing Sheets

(56) References Cited

U.S. PATENT DOCUMENTS

| | | | |
|---|---|---|---|
| 5,100,554 A | 3/1992 | Polaschegg | |
| 5,116,021 A | 5/1992 | Faust et al. | |
| 5,146,713 A | 9/1992 | Grafius | |
| 5,178,182 A | 1/1993 | Kamen | |
| 5,193,990 A | 3/1993 | Kamen et al. | |
| 5,211,201 A | 5/1993 | Kamen et al. | |
| 5,241,985 A | 9/1993 | Faust et al. | |
| 5,311,899 A | 5/1994 | Isayama et al. | |
| 5,324,422 A | 6/1994 | Colleran et al. | |
| 5,344,392 A | 9/1994 | Senninger et al. | |
| 5,350,357 A | 9/1994 | Kamen et al. | |
| D351,470 S | 10/1994 | Scherer et al. | |
| 5,353,837 A | 10/1994 | Faust | |
| 5,395,351 A | 3/1995 | Munsch | |
| 5,421,208 A | 6/1995 | Packard et al. | |
| 5,421,823 A | 6/1995 | Kamen et al. | |
| 5,431,626 A | 7/1995 | Bryant et al. | |
| 5,438,510 A | 8/1995 | Bryant et al. | |
| 5,447,286 A | 9/1995 | Kamen et al. | |
| 5,474,683 A | 12/1995 | Bryant et al. | |
| 5,486,286 A | 1/1996 | Peterson et al. | |
| 5,540,265 A | 7/1996 | Polaschegg et al. | |
| 5,570,716 A | 11/1996 | Kamen et al. | |
| 5,572,992 A | 11/1996 | Kankkunen et al. | |
| 5,583,948 A | 12/1996 | Shibayama | |
| 5,628,908 A | 5/1997 | Kamen et al. | |
| 5,634,896 A | 6/1997 | Bryant et al. | |
| 5,640,995 A | 6/1997 | Packard et al. | |
| 5,641,405 A | 6/1997 | Keshaviah et al. | |
| 5,641,892 A | 6/1997 | Larkins et al. | |
| 5,713,865 A | 2/1998 | Manning et al. | |
| 5,741,125 A | 4/1998 | Neftel et al. | |
| 5,755,683 A | 5/1998 | Houle et al. | |
| 5,771,914 A | 6/1998 | Ling et al. | |
| 5,772,637 A | 6/1998 | Heinzmann et al. | |
| 5,788,099 A | 8/1998 | Treu et al. | |
| 5,925,011 A * | 7/1999 | Faict et al. | 604/29 |
| 5,925,014 A | 7/1999 | Teeple Jr. | |
| 5,938,634 A | 8/1999 | Packard | |
| 5,989,423 A | 11/1999 | Kamen | |
| 5,997,502 A | 12/1999 | Reilly et al. | |
| 6,036,680 A | 3/2000 | Horne et al. | |
| 6,041,801 A | 3/2000 | Gray et al. | |
| 6,042,784 A | 3/2000 | Wamsiedler et al. | |
| 6,065,941 A | 5/2000 | Gray et al. | |
| 6,074,359 A | 6/2000 | Keshaviah et al. | |
| 6,118,207 A | 9/2000 | Ormerod et al. | |
| 6,126,831 A | 10/2000 | Goldau et al. | |
| 6,164,621 A | 12/2000 | Bouchard et al. | |
| 6,165,154 A | 12/2000 | Gray et al. | |
| 6,187,199 B1 | 2/2001 | Goldau | |
| 6,220,295 B1 | 4/2001 | Bouchard et al. | |
| 6,223,130 B1 | 4/2001 | Gray et al. | |
| 6,274,106 B1 * | 8/2001 | Held | 423/213.2 |
| 6,316,864 B1 | 11/2001 | Ormerod | |
| 6,343,614 B1 | 2/2002 | Gray et al. | |
| 6,364,857 B1 | 4/2002 | Gray et al. | |
| 6,382,923 B1 | 5/2002 | Gray | |
| 6,406,276 B1 | 6/2002 | Normand et al. | |
| 6,416,293 B1 | 7/2002 | Bouchard et al. | |
| 6,459,175 B1 | 10/2002 | Potega | |
| 6,468,424 B1 | 10/2002 | Doing et al. | |
| 6,497,676 B1 | 12/2002 | Childers et al. | |
| 6,503,062 B1 | 1/2003 | Gray et al. | |
| 6,520,747 B2 | 2/2003 | Gray et al. | |
| 6,558,343 B1 | 5/2003 | Neftel | |
| 6,592,542 B2 | 7/2003 | Childers et al. | |
| 6,595,944 B2 | 7/2003 | Balschat et al. | |
| 6,604,908 B1 | 8/2003 | Bryant et al. | |
| 6,614,008 B2 | 9/2003 | Tidrick | |
| 6,648,845 B1 | 11/2003 | Gotch et al. | |
| 6,663,359 B2 | 12/2003 | Gray | |
| 6,685,831 B2 | 2/2004 | Dönig et al. | |
| 6,702,774 B1 | 3/2004 | Polaschegg | |
| 6,709,417 B1 | 3/2004 | Houle et al. | |
| 6,726,656 B2 | 4/2004 | Kamen et al. | |
| 6,746,514 B2 | 6/2004 | Bedingfield et al. | |
| 6,749,403 B2 | 6/2004 | Bryant et al. | |
| 6,764,761 B2 | 7/2004 | Eu et al. | |
| 6,808,369 B2 | 10/2004 | Gray et al. | |
| 6,814,547 B2 | 11/2004 | Childers et al. | |
| 6,860,866 B1 | 3/2005 | Graf et al. | |
| 6,869,538 B2 | 3/2005 | Yu et al. | |
| 6,911,007 B2 | 6/2005 | Nier et al. | |
| 7,108,790 B2 * | 9/2006 | Collins et al. | 210/650 |
| 2002/0000793 A1 | 1/2002 | Hanaki | |
| 2002/0107474 A1 | 8/2002 | Noack | |
| 2002/0147423 A1 | 10/2002 | Burbank et al. | |
| 2003/0018395 A1 | 1/2003 | Crnkovich et al. | |
| 2003/0029451 A1 | 2/2003 | Blair et al. | |
| 2003/0085621 A1 | 5/2003 | Potega | |
| 2003/0111457 A1 | 6/2003 | Tidrick | |
| 2003/0130606 A1 | 7/2003 | Tuck | |
| 2003/0136189 A1 | 7/2003 | Lauman et al. | |
| 2003/0200812 A1 | 10/2003 | Kuhn et al. | |
| 2003/0204162 A1 | 10/2003 | Childers et al. | |
| 2003/0217957 A1 | 11/2003 | Bowman et al. | |
| 2003/0217961 A1 | 11/2003 | Hopping | |
| 2003/0217975 A1 | 11/2003 | Yu et al. | |
| 2003/0218623 A1 | 11/2003 | Krensky et al. | |
| 2003/0220599 A1 | 11/2003 | Lundtvcit et al. | |
| 2003/0220605 A1 | 11/2003 | Bowman et al. | |
| 2003/0220607 A1 | 11/2003 | Busby et al. | |
| 2003/0220608 A1 | 11/2003 | Huitt et al. | |
| 2003/0220609 A1 | 11/2003 | Childers et al. | |
| 2003/0220627 A1 | 11/2003 | Distler et al. | |
| 2004/0010223 A1 | 1/2004 | Busby et al. | |
| 2004/0019313 A1 | 1/2004 | Childers et al. | |
| 2004/0019320 A1 | 1/2004 | Childers et al. | |
| 2004/0031756 A1 | 2/2004 | Suzuki et al. | |
| 2004/0064080 A1 | 4/2004 | Cruz et al. | |
| 2004/0067161 A1 | 4/2004 | Axelsson | |
| 2004/0082903 A1 | 4/2004 | Micheli | |
| 2004/0122353 A1 | 6/2004 | Shahmirian et al. | |
| 2004/0135078 A1 | 7/2004 | Mandro et al. | |
| 2004/0195190 A1 | 10/2004 | Min et al. | |
| 2005/0151422 A1 | 7/2005 | Gilmour | |
| 2005/0230292 A1 | 10/2005 | Beden et al. | |
| 2005/0234381 A1 | 10/2005 | Niemetzer et al. | |
| 2005/0242034 A1 | 11/2005 | Connell et al. | |
| 2006/0195064 A1 | 8/2006 | Plahey et al. | |

FOREIGN PATENT DOCUMENTS

| | | | |
|---|---|---|---|
| WO | WO 92/11046 | | 7/1992 |
| WO | WO 92/18048 | * | 10/1992 |
| WO | WO 96/25214 | | 8/1996 |

OTHER PUBLICATIONS

Kidney International, vol. 66 (2004), pp. 1232-1238, Clinical consequences of an individualized dialysate sodium prescription in hemodialysis patients, Flavio M. DePaula, Aldo J. Peixoto, Luciano V. Pinto, David Dorigo, Pedro J.M. Patricio, and Sergrio F.F. Santos.

Kidney International, vol. 66, Supplement 89 (2004), pp. S1-S22, Mechanisms determining the ratio of conductivity clearance to urea clearance, Frank A. Gotch, Froilan M. Panlilio, Rosemary A. Buyaki, Erjun X. Wang, Thomas I Folden, and Nathan W. Levin.

Sleep Safe™ Operating Instructions, Fresenius Medical Care, Aug. 2000.

U.S. Appl. No. 29/224,370, filed Feb. 28, 2005, and entitled "Peritoneal Dialysis Cycler".

U.S. Appl. No. 29/224,371, filed Feb. 28, 2005, and entitled "Cassette for Peritoneal Dialysis Cycler".

U.S. Appl. No. 29/224,375, filed Feb. 28, 2005, and entitled "Peritoneal Dialysis Cycler".

Gambro®, "Prismaflex™ anticipating critical care needs and taking our innovative response . . . to new heights," © 2004, Gambro Inc., Lakewood, CO, 8 pp.

Gambro®, "DEHP-free cartridge blood sets," © Nov. 2004, Gambro, Inc., Lakewood, CO, 4 pp.

* cited by examiner

PERITONEAL DIALYSIS SYSTEMS AND RELATED METHODS

TECHNICAL FIELD

This invention relates to peritoneal dialysis systems and related methods.

BACKGROUND

Peritoneal dialysis can be used to support a patient whose renal function has decreased to the point where the kidneys no longer function sufficiently. During peritoneal dialysis, a peritoneal dialysis solution or dialysate is infused into the patient's abdominal cavity where it resides for a period of time. Diffusion and osmosis exchanges take place across the peritoneum (a membranous lining of the abdominal cavity) of the patient to remove waste products, such as urea and creatinine, from the patient's blood. The dialysate is then removed from the abdominal cavity of the patient along with the waste products.

SUMMARY

In one aspect of the invention, a method of performing peritoneal dialysis includes delivering first and second solutions to a mixing container. The first solution has a first concentration of a solute, and the second solution has a second concentration of the solute. The second concentration of the solute is different than the first concentration of the solute. The method also includes combining the first and second solutions in the mixing container to form a first dialysate having a concentration of the solute that is different than the first and second concentrations. The method further includes disposing the first dialysate in an abdominal cavity of a patient for a period of time, and removing the first dialysate from the abdominal cavity of the patient after the predetermined period of time.

In another aspect of the invention, a method of preparing a peritoneal dialysis solution includes delivering first and second solutions to a mixing container. The first solution has a first concentration of a solute, and the second solution has a second concentration of the solute. The second concentration of the solute is different than the first concentration of the solute. The method also includes combining the first and second solutions in the mixing container to form a dialysate having a concentration of the solute that is different than the first and second concentrations.

In a further aspect of the invention, a peritoneal dialysis system includes a first container containing a first solution, a second container containing a second solution, a mixing container in fluid communication with the first and second containers, and a pump configured to pump metered amounts of the first and second solutions to the mixing container to form a dialysate. The first solution has a first concentration of a solute, and the second solution has a second concentration of the solute.

In an additional aspect of the invention, a method of peritoneal dialysis treatment includes automatically custom blending at least two pre-packaged peritoneal dialysis solutions of differing formulations according to proportions controlled by a peritoneal dialysis machine based on a prescription for a given patient. The method further includes warming the blended peritoneal dialysis solutions, and filling a patient's abdominal cavity with the warmed blended peritoneal solutions for a period of time to perform at least a portion of a peritoneal dialysis treatment.

Implementations can include one or more of the following features.

In some implementations, the peritoneal dialysis system further includes a control unit in communication with the pump. The control unit is adapted to control the amounts of the first and second solutions that are pumped to the mixing container.

In certain implementations, the first solution is delivered to the mixing container from a first supply bag.

In some implementations, delivering the first solution from the first supply container to the mixing container includes pumping the first solution through a line that fluidly connects the first supply container to the mixing container.

In certain implementations, the second solution is delivered to the mixing container from a second supply bag.

In some implementations, delivering the second solution from the second supply container to the mixing container includes pumping the second solution through a line that fluidly connects the second supply container to the mixing container.

In certain implementations, the mixing container is a heater bag.

In some implementations, the heater bag is in contact with a heating element such that the dialysate within the heater bag can be heated by the heating element.

In certain implementations, the mixing container is a fluid line.

In some implementations, the fluid line is in fluid communication with the abdominal cavity of the patient.

In certain implementations, the fluid line includes a flash heater.

In some implementations, the dialysate is heated within the fluid line prior to being disposed within the abdominal cavity of the patient.

In certain implementations, the solute is dextrose.

In some implementations, the solute is calcium.

In certain implementations, the solute is magnesium.

In some implementations, the first solution is a dialysate (e.g., a commercially available, pre-packaged dialysate).

In certain implementations, the second solution is a dialysate (e.g., a commercially available, pre-packaged dialysate).

In some implementations, the first solution is a dialysate concentrate.

In certain implementations, the second solution is reverse osmosis water.

In some implementations, delivering the first and second solutions to the mixing container includes delivering predetermined volumes of the first and second solutions to the mixing container.

In certain implementations, a pump is actuated in a manner to deliver the predetermined volumes of the first and second solutions to the mixing chamber.

In some implementations, the pump is in communication with a control unit adapted to control a displacement of the pump, and a volume of the first and second solution delivered by the pump is proportional to the displacement of the pump.

In certain implementations, the method further includes determining the predetermined volumes of the first and second solutions based on a desired concentration of the solute in the dialysate.

In some implementations, the method further includes delivering the first and second solutions to the mixing container to form a second dialysate having a concentration of the solute that differs from the concentration of the solute in the first dialysate. The method also includes disposing the second dialysate in the abdominal cavity of the patient for a period of time, and removing the second dialysate from the abdominal cavity of the patient after the predetermined period of time.

In certain implementations, respective volumes of the first and second solutions delivered to the mixing container to form the second dialysate differ from respective volumes of the first and second solutions delivered to the mixing container to the form the first dialysate.

In some implementations, the concentration of the solute in the second dialysate is less than the concentration of the solute in the first dialysate.

In certain implementations, the method further includes delivering the first and second solutions to the mixing container to form a third dialysate having a concentration of the solute that differs from the concentrations of the solute in the first and second dialysates. The method further includes disposing the third dialysate in the abdominal cavity of the patient for a period of time, and removing the third dialysate from the abdominal cavity of the patient after the predetermined period of time.

In some implementations, respective volumes of the first and second solutions delivered to the mixing container to form the third dialysate differ from respective volumes of the first and second solutions delivered to the mixing container to the form the first and second dialysates.

In certain implementations, the control unit is adapted to control the amounts of the first and second solutions that are pumped to the mixing container based on a desired concentration of the solute in a dialysate to be formed in the mixing container upon combining the first and second solutions.

In some implementations, the control unit is adapted to receive input data.

In certain implementations, the control unit is adapted to control amounts of the first and second solutions that are pumped to the mixing container based on the input data.

In some implementations, the input data comprises a dialysate prescription.

In certain implementations, the pump includes a stepper motor.

Implementations can include one or more of the following advantages.

In some implementations, custom dialysates (i.e., dialysates having concentrations of one or more solutes different than those concentrations that are typically found, e.g., in commercially available, pre-packaged dialysates) are produced. The custom dialysates can, for example, be produced by mixing or blending desired amounts of two or more commercially available, pre-packaged dialysates. As a result, physicians can prescribe dialysates with solute concentrations that are best-suited for particular patients rather than being limited to selecting from commercially available, pre-packaged dialysates, which may have formulations, e.g., solute concentrations, that differ substantially from the ideal formulations for treatment of particular patients.

In certain implementations, the custom dialysates are used to perform peritoneal dialysis. Using such custom dialysates permits peritoneal dialysis treatments to be tailored to the medical conditions of specific patients. As a result, the efficiency of the peritoneal dialysis treatments can be increased. In some cases, the comfort level of the patient (e.g., during treatment and/or after treatment) can also improve.

In some implementations, multiple different custom dialysates are used during a peritoneal dialysis treatment. For example, multiple dialysates with gradually decreasing concentrations of one or more solutes can be sequentially used during the treatment. By deploying different custom dialysates in this manner, the effects of the dialysis treatment (e.g., the rate at which water and/or waste products are removed from the patient's blood) can be varied or profiled over the course of the treatment, for example, gradually decreased as the treatment progresses, in a manner specifically prescribed for the patient. In certain implementations, for example, custom dialysates having gradually decreasing concentrations of dextrose (also known as "glucose") are delivered to the patient throughout the treatment. As a result, relatively large amounts of water are removed from the patient in the early stages of the treatment, while relatively small amounts of water are removed from the patient in the later stages of the treatment. This technique can help to rapidly relieve the patient of discomfort associated with having retained excessive amounts of water since the last treatment, and can help to prevent negative side effects that can result from the removal of excessive amounts of water in the later stages of the treatment. Gradually decreasing dextrose concentrations of dialysates used during the treatment can alternatively or additionally help to reduce reabsorption of dextrose in the patient between treatments. In some implementations, for example, at least some of the dialysate that is delivered to the patient during the last cycle of treatment remains in the patient between treatments. In such implementations, using a dialysate having a low concentration dextrose during the last cycle of treatment can help to reduce the amount dextrose reabsorbed by the patient between treatments.

In certain implementations, the peritoneal dialysis systems are capable of producing dialysates having a variety of different concentrations of one or more solutes using a highly concentrated dialysis solution (e.g., a dialysate concentrate). The peritoneal dialysis systems can, for example, include a supply of liquid (e.g., a supply of reverse osmosis water and/or sterile saline) that can be mixed with the highly-concentrated dialysis solution to produce dialysates having a variety of different concentrations. This arrangement can enable the physician to prescribe dialysates having a wide variety of concentrations, over multiple treatments, or during the course of a single treatment, without the need for a wide variety of different commercially available dialysates. As a result, the cost-efficiency of treatments can increase, and the inconvenience associated with storing and using a large number of different dialysates can be alleviated, along with the production of a wider variety of FDA approved pre-packaged solutions.

In some implementations, a solution is added to a dialysate (e.g., a commercially available, pre-packaged dialysate) to form a custom dialysate. The solution can, for example, include one or more substances (e.g., one or more drugs, nutritional supplements, vitamins, etc.) to be absorbed by the patient during treatment. This can be beneficial when a patient has insufficient levels of one or more substances in his/her body. In such cases, in addition to removing excess water and/or waste products from the patient's blood, the custom dialysate can be used to replenish diminished levels of one or more substances in the patient's body.

Other aspects, features, and advantages will be apparent from the description and drawings, and from the claims.

DESCRIPTION OF DRAWINGS

Like reference symbols in the various drawings indicate like elements.

DETAILED DESCRIPTION

This disclosure relates to peritoneal dialysis systems and related methods. The systems and methods can be used to produce custom dialysates having concentrations of one or more solutes that are different than concentrations of those one or more solutes that are typically found in commercially available dialysates. In some implementations, custom dialysates are formed by combining desired amounts of two or more dialysates (e.g., two or more commercially available, pre-packaged dialysates). In certain implementations, custom dialysates are formed by combining or blending a highly-concentrated dialysis solution (e.g., a dialysate concentrate) with a desired amount of a liquid, such as reverse osmosis water and/or sterile saline. Examples of peritoneal dialysis systems and related methods are described below.

The methods described herein can be implemented using a peritoneal dialysis cycler of the type disclosed in U.S. patent application Ser. No. 11/069,195, filed Feb. 28, 2005 and entitled "Portable Apparatus for Peritoneal Dialysis Therapy," which is incorporated by reference herein. The referenced cycler allows a dialysis patient to be treated at home instead of or in addition to visiting a dialysis clinic where hemodialysis is performed. However, this is only one example of the type of equipment that can be used to carry out the methods described herein, as it is possible for the methods disclosed herein to be carried out on other types of systems as well, including but not limited to gravity feed systems and other cycler-type systems.

Figure 1:
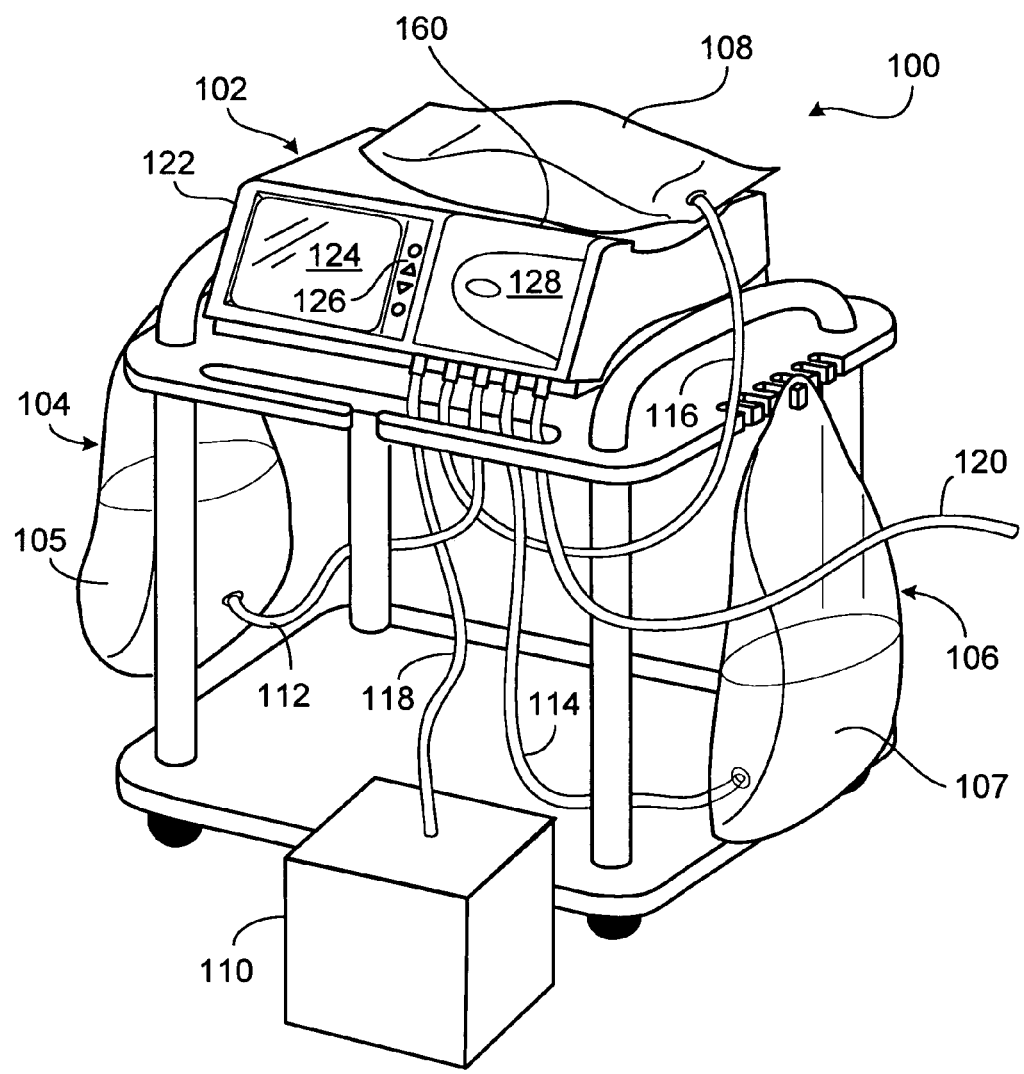
FIG. 1 is a diagrammatic perspective view of a peritoneal dialysis system.

Referring to FIG. 1, a peritoneal dialysis system 100 includes a peritoneal dialysis machine 102, dialysate supply or "source" bags 104 and 106, a heater bag 108, and a drain container 110. Dialysate supply bags 104 and 106 are fluidly connected to a peritoneal dialysis cycler 102 by supply lines 112 and 114, respectively. Dialysate supply bag 104 contains a first dialysate 105, and dialysate supply bag 106 contains a second dialysate 107. As discussed below, first and second dialysates 105 and 107 include different concentrations of one or more solutes (e.g., different concentrations of dextrose, magnesium, and/or calcium). Heater bag 108 is fluidly connected to dialysis machine 102 by heater line 116. Drain container 110 is fluidly connected to dialysis machine 102 by drain line 118. A patient line 120 is also fluidly connected to dialysis machine 102. During peritoneal dialysis treatments, as discussed below, the end of patient line 120 opposite dialysis machine 102 can be fluidly connected to a patient's abdominal cavity (e.g., by connecting patient line 120 to a peritoneal dialysis catheter disposed through the patient's abdominal wall), allowing fluid (e.g., dialysate and/or body fluid) to flow to and from the patient's abdominal cavity.

Figure 2:
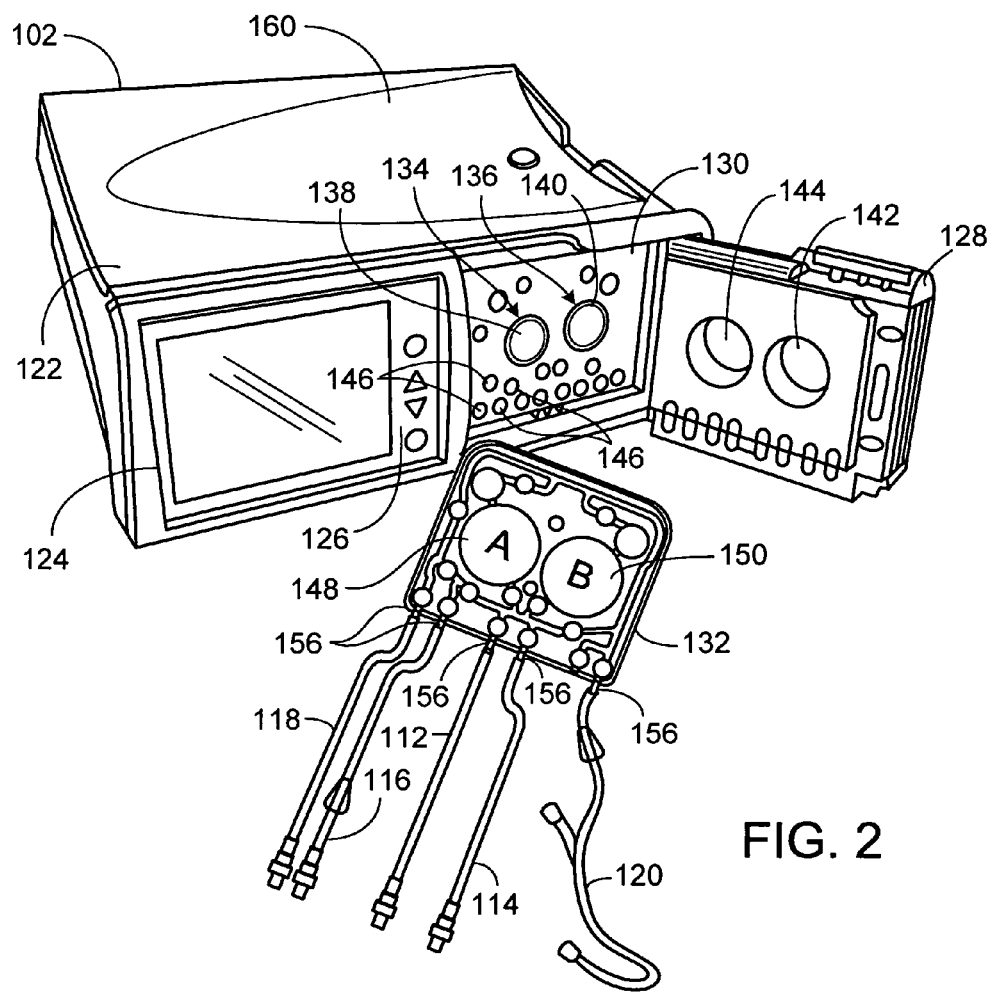
FIG. 2 is a compound perspective, partially exploded view of the peritoneal dialysis system of FIG. 1, showing a peritoneal dialysis cycler and a cassette for installation into a cassette compartment of the peritoneal dialysis cycler.

Referring to FIGS. 1 and 2, dialysis machine 102 includes a housing 122 that holds an LCD display with a touch screen overlay 124, along with additional control buttons 126 collectively constituting a user interface or control panel that can be manipulated by the user (e.g., the patient) to control dialysis machine 102. Touch screen 124 and/or control buttons 126 can, for example, be used to input data to a control unit (not shown) disposed within housing 122. The control unit can then operate dialysis machine 102 according to the inputted data entries or "therapy settings," as will be discussed in more detail below.

Housing 122 also includes a side-hinged door 128 and a cassette support deck 130 forming a cassette compartment configured to support and contain a cassette (e.g., a disposable cassette) 132. Two recesses 142 and 144 are formed within door 128. Cassette support deck 130 includes two pumps 134 and 136, which include exposed mushroom-shaped pump heads 138 and 140, respectively. Pumps 134 and 136 are configured such that pump heads 138 and 140 align with recesses 142 and 144, respectively, of hinged door 128 when hinged door 128 is closed.

Pumps 134 and 136 are driven by stepper motors and drive mechanisms (not shown). When actuated, the stepper motors cause pump heads 138 and 140 to move into and out of recesses 142 and 144, respectively, of hinged door 128 by precisely controlled displacements. The stepper motors operate by driving conventional lead screws (not shown) which move nuts (not shown) inward and outward on the lead screws. The nuts, in turn, are connected to pump heads 138, 140. The stepper motor and lead screw are chosen to provide the required force to push fluid out of cassette 132 following the opening of fluid paths in cassette, as will be described later. The stepper motor preferably requires 200 steps to make a full rotation, and this corresponds to 0.048" of linear travel. Additionally, an encoder measures the angular movement of the lead screw. This measurement can be used to very accurately position pump heads 138 and 140.

The stepper motors of pumps 134 and 136 can be controlled by stepper motor controllers (not shown) that are in electrical communication with the stepper motors and are capable of providing current to energize the windings of the stepper motors. The polarity of the current determines whether pump heads 138 and 140 move forward or backward.

Support deck 130 for the cassette compartment also includes multiple balloon valves 146. Balloon valves 146 are fluidly connected to a pneumatic system (not shown) disposed within dialysis machine 122. The pneumatic system includes a compressor pump (not shown) that can be used to provide either air or vacuum to the reservoirs in which balloon valves 146 reside. As a result, balloon valves 146 can be inflated and deflated by the compressor pump during use. As discussed below, balloon valves 146 can cooperate with cassette 132 to direct fluid flow through cassette 132 in a desired manner.

Cassette 132 is sized and shaped to fit into the cassette compartment. Cassette 132 can be inserted into the compartment by sliding it into contact with registration pins and a lower support tab (not shown) on the support deck 130 and door 128 can be closed upon cassette 132 to securely retain cassette 132 between support deck 130 and door 128. In some implementations, an inflatable pad (not shown) is provided in door 128 and can be inflated to force cassette 132 against support deck 130 when door 128 is closed. The inflatable pad can, for example, be inflated using the compressor pump of the pneumatic system in dialysis machine 102.

Figure 3:
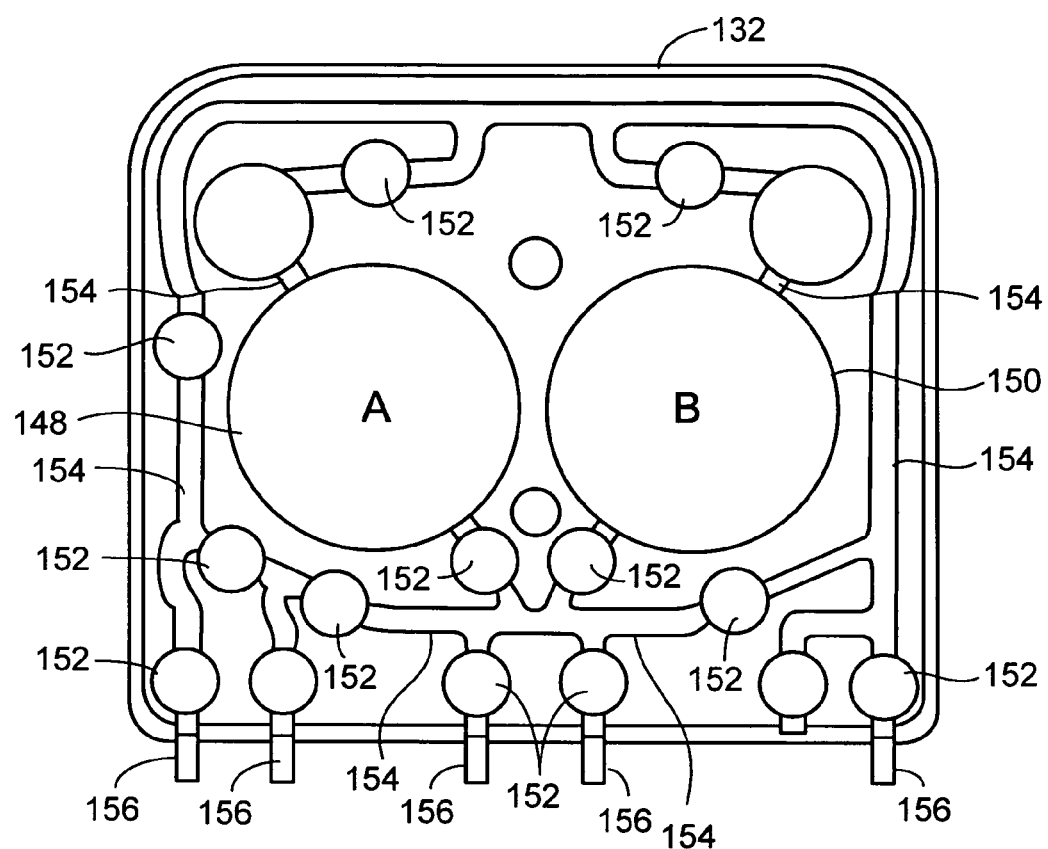
FIG. 3 is an enlarged view of the cassette of FIG. 2.

FIG. 3 is an enlarged view of cassette 132. Referring to FIG. 3, cassette 132 is a polymeric member with two fluid chambers A and B partially formed by flexible diaphragms 148 and 150, respectively. Diaphragms 148 and 150 mate with recesses 142 and 144, respectively, of door 128 and with pumps 134 and 136, respectively, of cassette support deck 130 when cassette 132 is disposed on cassette support deck 130 and door 128 is closed. Cassette 132 also includes a relatively rigid back with two hollow, dome-shaped protrusions (not shown) extending therefrom. These protrusions are positioned opposite diaphragms 148 and 150 to fully define chambers A and B. The protrusions are shaped to receive pump heads 138 and 140, respectively, and can be at least partially disposed within recesses 142 and 144 when door 128 is closed. Multiple fluid passages 154 extend within cassette 132. Fluid passages 154 fluidly connect chambers A and B to inlets/outlets 156 of cassette 132. Multiple buttons or diaphragms 152 are positioned along fluid passages 154. Buttons 152 are depressible, hollow members and are positioned to connect one section of fluid passage 154 to an adjacent section of fluid passage 154. Buttons 152 align with balloon valves 146 of support deck 130 when cassette 132 is disposed within support deck 130. During use, balloon valves 146 can be inflated to depress buttons 152 to prevent fluid flow through those regions of fluid passages 154 in which the depressed buttons 152 are located. Similarly, balloon valves 146 can be deflated to allow buttons 152 to expand and to allow fluid to flow through those regions of fluid passages 154 in which the expanded buttons 152 are located. Typically, some balloon valves 146 are inflated while other balloon valves 146 are deflated, thereby allowing fluid to flow through some sections of fluid passages 154 and preventing the flow of fluid through other sections of fluid passages 154. For example, the direction of flow into and out of chambers A and B is determined by whether the lower or upper adjacent button 152 is depressed when pump heads 138 and 140 stroke inward compressing respective diaphragms 148 and 150 on cassette 132. In this manner, fluid can be drawn from a desired source and can be delivered to a desired source during use. In addition, pumps 134 and 136 can be controlled (e.g., by the control unit of dialysis machine 102) to draw a desired volume of fluid from a desired source and to deliver a desired volume of fluid to a desired source.

Referring again to FIGS. 1 and 2, a heater tray 160 is disposed on top of housing 122 of dialysis machine 102. Heater tray 160 is configured so that, during use, heater bag 108 can rest on heater tray 160. Heater tray 160 includes heater coils extending threrethrough and a temperature sensor. By activating the heater coils within heater tray 160 under thermostatic control, heater bag 108 and its contents can be warmed to a predetermined temperature.

First dialysate supply bag 104, second dialysate supply bag 106, heater bag 108, and drain container 110 are fluidly connected to cassette 132 by fluid lines 112, 114, 116, and 118, respectively. Fluid lines 112, 114, 116, and 118 can, for example, be connected to fluid inlets/outlets 156 of cassette 132.

Supply bags 104 and 106 can contain a sufficient volume of dialysates 105 and 107, respectively, to perform a complete peritoneal dialysis treatment. For example, supply bags 104 and 106 can contain from about five liters to about 20 liters of dialysate. As noted above, dialysates 105 and 107 have different concentrations of one or more solutes. Dialysate 105 has a dextrose concentration of about 1.5 percent, and dialysate 107 has a dextrose concentration of about 4.25 percent. Dialysates 105 and 107 can be commercially available, pre-packaged peritoneal dialysis solutions, such as DELFLEX® dextrose peritoneal dialysis solutions.

While only two supply bags 104 and 106 are shown by way of example in FIG. 1, any reasonable number of solution bags is possible. The main constraint on the size and number of bags generally relates to storage and handling by patients and the total volume of dialysate desired or prescribed for treatment. In some implementations, four supply bags are provided. Two of the supply bags can, for example, contain dialysate with a dextrose concentration of about 1.5 percent, and the other two supply bags can contain a dialysate with a dextrose concentration of about 4.25 percent. In such implementations, heater bag 108 can be provided in addition to these supply bags and can contain a solution (e.g., a dialysate) when placed on heater tray at the beginning of the treatment for the first fill.

Figure 4A:
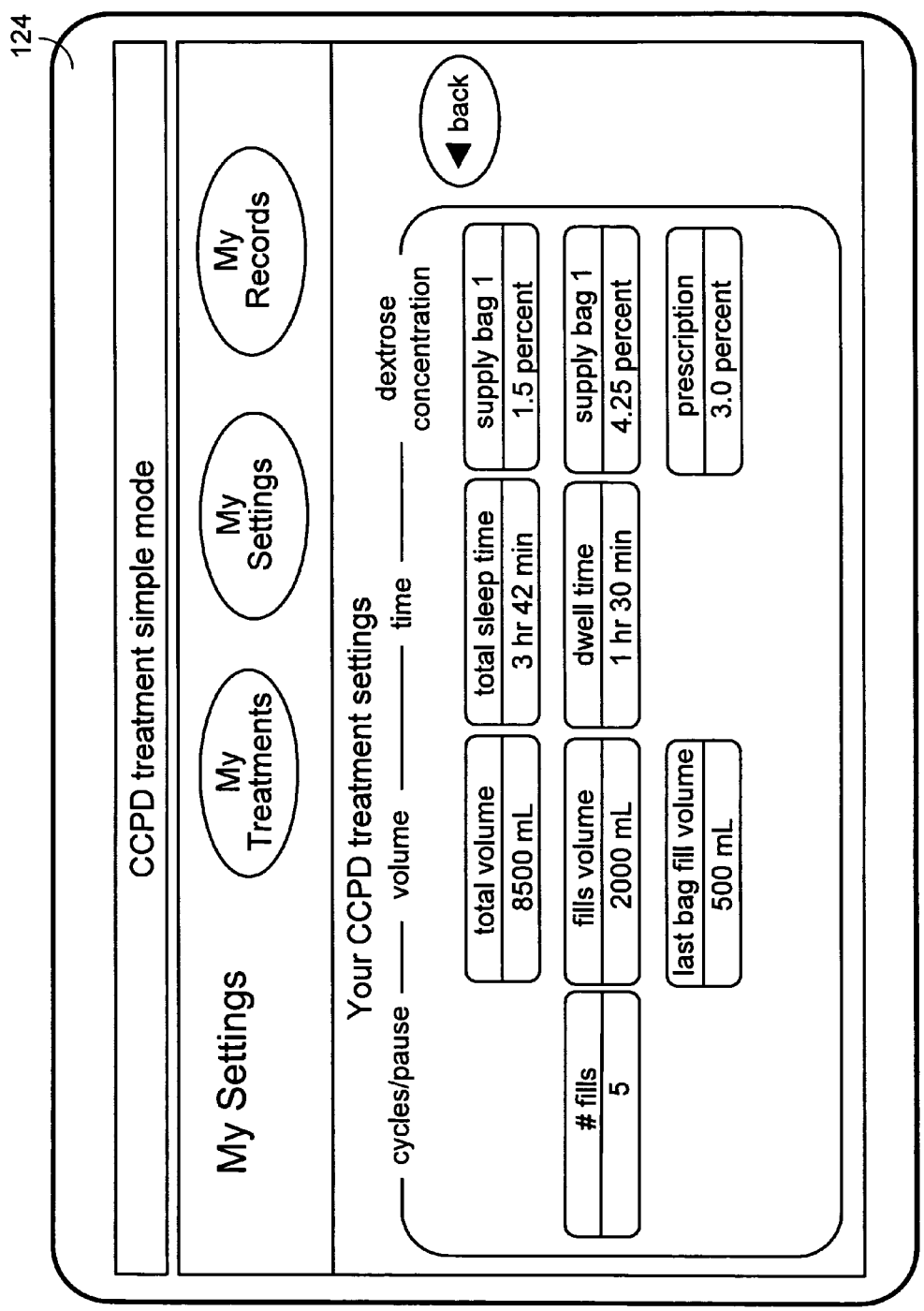
FIGS. 4A-4D are diagrams illustrating a method of using the peritoneal dialysis system of FIGS. 1 and 2.

FIGS. 4A-4D illustrate a method of using dialysis system 100 to treat a patient 200. Referring to FIG. 4A, to begin the peritoneal dialysis treatment, data is input into dialysis machine 102 using touch screen 124 and/or control buttons 126. Among other things, the data input to dialysis machine 102 includes the dextrose concentration of dialysate prescribed for the patient being treated, the dextrose concentrations of dialysates 105 and 107 (i.e., the dextrose concentration of the dialysates contained in supply bags 104 and 106), the fill volume (i.e., the volume of dialysate to be delivered to the patient during each cycle), and the total number of fills (i.e., the total number of times the dialysate will be delivered to the patient during treatment). As shown by touch screen 124 in the embodiment shown in FIG. 4A, the user has input data to indicate that supply bag 104 includes a dialysate with a 1.5 percent dextrose concentration, supply bag 106 includes a dialysate with a 4.25 dextrose concentration, the prescribed dextrose concentration is 3.0 percent, the peritoneal dialysis treatment will include five fills, and each fill (with the exception of the last fill) will include the delivery of 200 mL of dialysate to the patient.

Figure 4B:
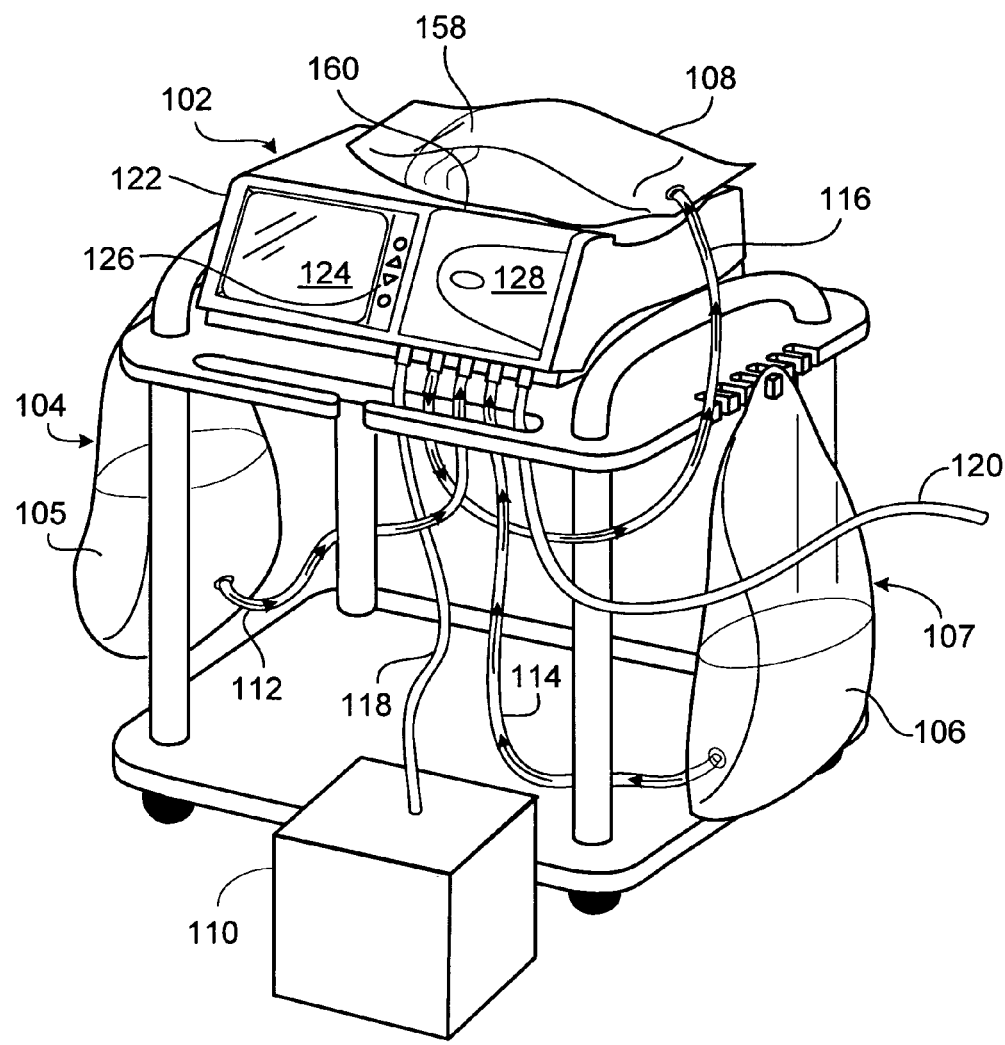

Referring to FIG. 4B, based on this input data, desired amounts of dialysate 105 and dialysate 107 are delivered to heater bag 108 where they are combined to form a custom dialysate 158. The control unit of dialysis machine 102, which is in communication with touch screen 124 as well as pumps 134 and 136 (e.g., stepper motor controllers of pumps 134 and 136), determines the ratio of dialysates 105 and 107 required to be delivered to heater bag 108 to ensure that custom dialysate 158 has the prescribed dextrose concentration. In this case, to ensure that custom dialysate 158 has the prescribed dextrose concentration input by the user (i.e., 3.0 percent dextrose), the control unit calculates that dialysates 105 and 107 need to be delivered to heater bag 108 at a ratio of 1:2. The control unit then transmits data signals to the stepper motor controllers that control pumps 134 and 136 and to the pneumatic system that controls balloon valves 146, causing pumps 134 and 136 and balloon valves 146 to be operated in a manner to deliver dialysates 105 and 107 to heater bag 108 at the desired ratio of 1:2. As a result, custom dialysate 158 is produced within heater bag 108 with a dextrose concentration of about 3.0 percent.

By mixing dialysates 105 and 107, which have different concentrations of dextrose, custom dialysate 158 can be formed to have a dextrose concentration intermediate to the dextrose concentrations of dialysates 105 and 107. Custom dialysate 158 can, for example, have a dextrose concentration that is not typically found in commercially available, pre-packaged dialysates.

In addition to controlling the ratio of dialysates 105 and 107 delivered to heater bag 108, the control unit also transmits data signals to pumps 134 and 136 related to the volume of dialysates 105 and 107 to be delivered to heater bag 108. This value can be determined based on the ratio at which dialysates 105 and 107 are to be delivered to heater bag 108 and the fill volume that was input by the patient. In the implementation shown, pumps 134 and 136 and balloon valves 146 are operated to deliver 667 mL of dialysate 105 and 1333 mL of dialysate 107 to heater bag 108 to produce 200 mL of custom dialysate 158.

Referring again to FIG. 2, in order to deliver dialysates 105 and 107 from supply bags 104 and 106 to heater bag 108, pumps 134 and 136 and balloon valves 146 are operated in a manner to draw dialysate 105 and dialysate 107 into chambers A and B of cassette 132, and after drawing dialysates 105 and 107 into chambers A and B of cassette 132, pumps 134 and 136 and balloon valves 146 are operated in a manner to force dialysates 105 and 107 out of chambers A and B and into heater bag 108. To draw dialysates 105 and 107 into chambers A and B, pumps 134 and 136 are pulled back by their associated stepper motors and, at the same time, a vacuum is created behind diaphragms 148 and 150 of cassette 132 so as to retract diaphragms 148 and 150. Pumps 134 and 136 can, for example, reside within vacuum chambers with a small amount of clearance extending circumferentially around pump heads 138 and 140, between the outer circumferences of pump heads 138 and 140 and the inner surface of the respective vacuum chambers in which they reside. As a result, when a vacuum is created within the vacuum chambers, suction may be applied to diaphragms 148 and 150 via the circumferential passages between pump heads 138 and 140 and the inner surfaces of the respective vacuum chambers in which they reside. While retracting pumps 134 and 136, balloon valves 146 are operated in a manner to permit dialysates 105 and 107 to flow into chambers A and B of cassette 132 from supply bags 104 and 106. For example, those balloon valves 146 corresponding to buttons 152 within the fluid passages connecting fluid line 112 to chamber A and connecting fluid line 114 to chamber B can be deflated while all other balloon valves 146 are inflated. The retraction of diaphragms A and B causes dialysate 105 to be drawn into chamber A from dialysate supply bag 104 and causes dialysate 107 to be drawn into chamber B from dialysate supply bag 106.

After drawing dialysates 105 and 107 into chambers A and B, respectively, pumps 134 and 136 are used to force dialysates 105 and 107 out of cassette 132 and into heater bag 108. To force dialysates 105 and 107 out of chambers A and B, respectively, pumps 134 and 136 are extended, moving pump heads 138 and 140 substantially all the way to the wall of the relatively rigid back of cassette 132 (without contacting the wall). The displacement of pump heads 138 and 140 causes dialysates 105 and 107 to be ejected from chambers A and B and into heater bag 108 via those fluid passages 154 that connect chambers A and B to heater bag 108.

Typically, pumps 134 and 136 and balloon valves 146 are operated to separately deliver dialysates 105 and 107 to heater bag 108. For example, pumps 134 and 136 and balloon valves 146 can be operated to deliver a desired volume of dialysate 105 to heater bag 108, and, after delivering the desired volume of dialysate 105 to heater bag 108, pumps 134 and 136 and balloon valves 146 can be operated to deliver a desired volume of dialysate 107 to heater bag 108, or vice versa. While drawing dialysate 105 from supply bag 104, button 152 adjacent inlet/outlet 156 leading to supply bag 106 is depressed to prevent dialysate 107 from being drawn into chamber A and/or chamber B along with dialysate 105. After a desired amount of dialysate 105 has been delivered to heater bag 108, button 152 adjacent inlet/outlet 156 leading to supply bag 104 is depressed and button 152 adjacent inlet/outlet 156 leading to supply bag 106 is released, allowing dialysate 107 to be drawn into chamber A and/or chamber B and preventing dialysate 105 from being drawn into chamber A and/or chamber B.

Pumps 134 and 136 are typically operated using an alternating pumping method such that some of the dialysate is drawn into chamber A, and, at the same time, some of the dialysate is forced out of chamber B, and vice versa. For example, while retracting pump 134, button 152 located between dialysate bag 104 and chamber A can be released and button 152 located between chamber A and heater bag 108 can be depressed, allowing dialysate 105 to be drawn into chamber A. At the same time, pump 136 can be extended while button 152 located between dialysate bag 104 and chamber B is depressed and button 152 located between chamber B and heater bag 108 is released, allowing dialysate 105, which was previously drawn into chamber B, to be delivered to heater bag 108. This pumping method can be repeated until a desired volume of dialysate 105 has been delivered to heater bag 108. Subsequently, a similar pumping method can be employed to deliver a desired volume of dialysate 107 to heater bag 108.

Pumps 134 and 136 can alternatively be operated in tandem such that the dialysate is simultaneously drawn into chambers A and B and then simultaneously forced out of chambers A and B. For example, while all buttons 152 except for the button adjacent inlet/outlet 156 leading to supply bag 104 are depressed, pumps 134 and 136 are simultaneously retracted to draw dialysate 105 into chambers A and B. After drawing dialysate 105 into chambers A and B, button 152 adjacent inlet/outlet 156 leading to supply bag 104 is depressed and buttons 152 adjacent the outlets of chambers A and B are released. Pumps 134 and 136 are then extended, forcing dialysate 105 from chambers A and B into heater bag 108. This technique is repeated until the desired amount of dialysate 105 resides in heater bag 108. At that point, a similar technique is performed to transfer a desired amount of dialysate 107 from supply bag 106 to heater bag 108.

As noted above, the ratio of dialysates 105 and 107 used to form custom dialysate 158 can be controlled by controlling the volume of dialysates 105 and 107 delivered to heater bag 108, which is dictated by the operation of pumps 134 and 136, respectively. Because the volumes of cassette 132 and pump heads 138 and 140 are known values (based on their known physical dimensions), the amount by which pump heads 138 and 140 need to be displaced in order to draw a predetermined volume of dialysates 105 and 107 into chambers A and B or to force a predetermined volume of dialysates 105 and 107 out of chambers A and B can be readily determined. For example, if pump heads 138 and 140 are flush against the cassette wall, then substantially no fluid volume can reside in cassette chambers A and B. As pump heads 138 and 140 are retracted from recesses 142 and 144 along with diaphragms 148 and 150, however, they draw dialysates 105 and 107 into chambers A and B of cassette 132. The volume of dialysates 105 and 107 drawn into chambers A and B can be calculated by subtracting the volume of pump heads 138 and 140 that remain in chambers A and B from the total volume of chambers A and B. To calculate how much volume of pump heads 138 and 140 reside inside chambers A and B, the amounts of linear travel of pumps 134 and 136 can be calculated. These distances correlate to the distances of travel of pump heads 138 and 140. From those distances, a formula can be used to determine how much fluid volume still resides in chambers A and B. By using this information, pumps 134 and 136 can be programmed to accurately deliver desired volumes of dialysates 105 and 107 to heater bag 108. For example, the control unit of dialysis machine 102, based on the above-discussed volumetric data of pumps 134 and 136 and the data input to touch screen 124 by the patient, can cause pumps 134 and 136 to deliver the desired volumes of dialysates 105 and 107 to ensure that custom dialysate 158 has the prescribed concentration of dextrose and to ensure that the desired volume of custom dialysate 158 is produced.

Pumps 134 and 136 can be configured to accurately draw the desired volume of dialysates 105 and 107 from supply bags 104 and 106 and to accurately deliver desired amounts of dialysates 105 and 107 to heater bag 108. As discussed above, for example, the stepper motors of pumps 134 and 136 can require 200 steps to make a full rotation, which corresponds to about 0.048 inch of linear travel. As a result, pump heads 138 and 140 can be precisely actuated and the volume of fluid displaced by pump heads 138 and 140 can be accurately controlled. While drawing dialysate into chambers A and B and expelling dialysate from chambers A and B, pumps 134 and 136 can be actuated in less than a full stroke. For example, where making custom dialysate 158 requires delivering dialysate 105 and/or dialysate 107 to heater bag 108 in volumes less than the capacity of chambers A and B, pumps 134 and 136 can be moved a fraction of a stroke. This ability can enable the production of custom dialysates having an accurate concentration of dextrose.

After or while delivering the desired volumes of dialysates 105 and 107 to heater bag 108 to form custom dialysate 158, custom dialysate 158 is heated to a desired temperature (e.g., approximately the body temperature of the patient). Custom dialysate 158 is heated by activating heater tray 160 on which heater bag 108 rests. Heater tray 160 and/or heater bag 108 can include a temperature sensor to detect the temperatures of heater tray 160 and/or custom dialysate 158 within heater bag 108. The temperature sensor can, for example, be in communication with a control unit that controls the operation of heater tray 160. Thus, heater tray 160 can be controlled to ensure that custom dialysate 158 is heated to and maintained at a desired temperature (e.g., the body temperature of the patient) during the peritoneal dialysis treatment.

Figure 4C:
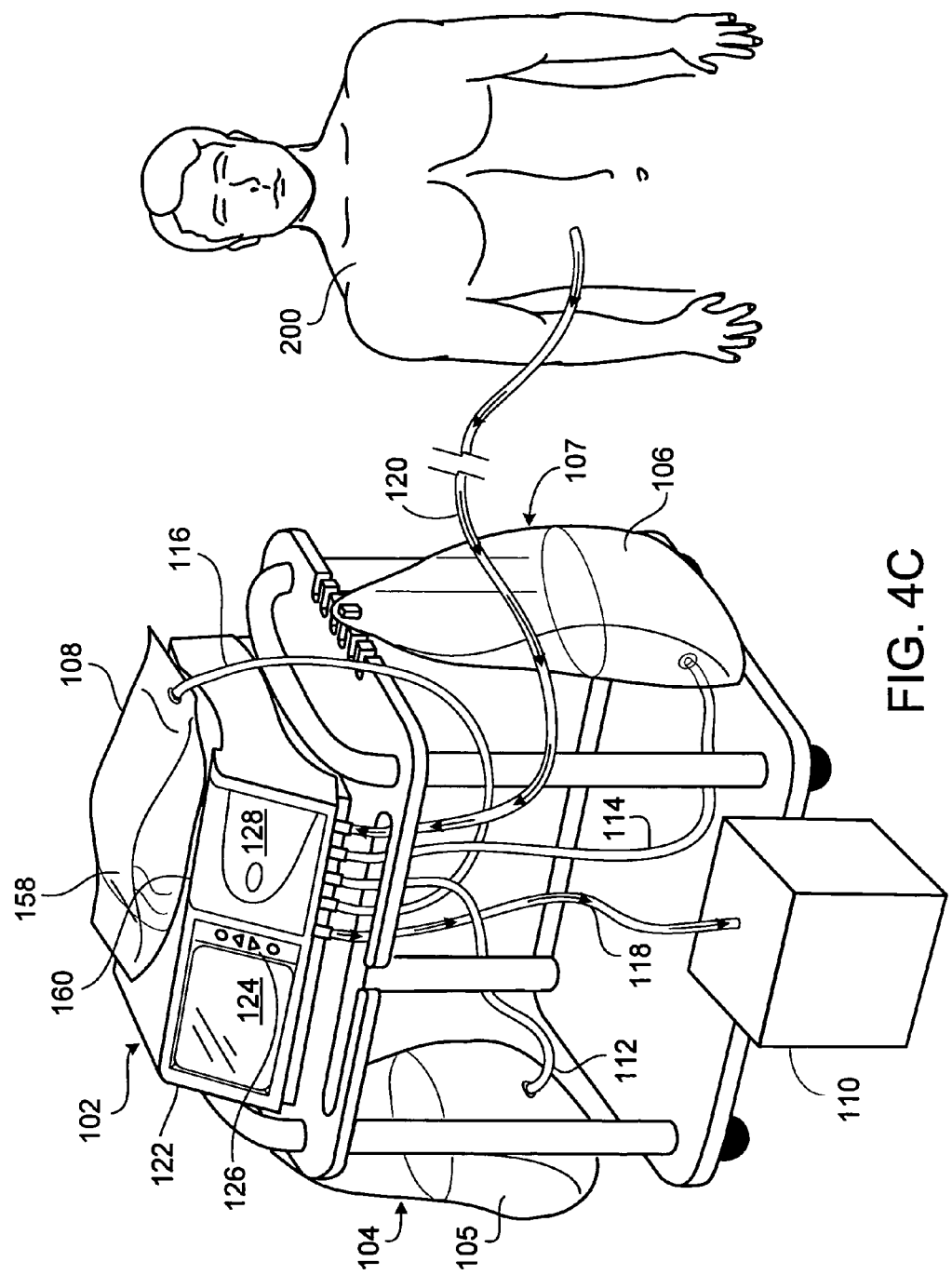

Referring to FIG. 4C, while heating custom dialysate 158, patient line 120 is connected to a patient 200, and a drain sequence is performed to remove fluid (e.g., body fluid and/or residual dialysate from the last peritoneal dialysate treatment) from patient 200. During the drain sequence, fluid is drawn from the abdominal cavity of patient 200 and into cassette 132 via patient line 120. The fluid is then pumped from cassette 132 to drain container 110 via drain line 118. To draw the fluid from patient 200 into cassette 132, an alternating pumping method is typically employed. During the alternating pumping method, one of pumps 134 and 136 is retracted while the other of pumps 134 and 136 is extended. For example, as pump 134 is retracted from recess 146 to draw fluid from patient 200 into chamber A via patient line 120, pump 136 is extended within chamber A causing the fluid in chamber B to be forced out into drain line 118. When this motion is completed, pump 136 is then retracted, drawing fluid from patient 200 into chamber B, and pump 134 is extended, forcing fluid from chamber A into drain line 118. This process can continue until a desired volume of fluid has been removed from patient 200. Pumps 134 and 136 can alternatively be operated in tandem to draw the fluid from patient 200 and to deliver the drawn fluid to drain container 110.

Figure 4D:
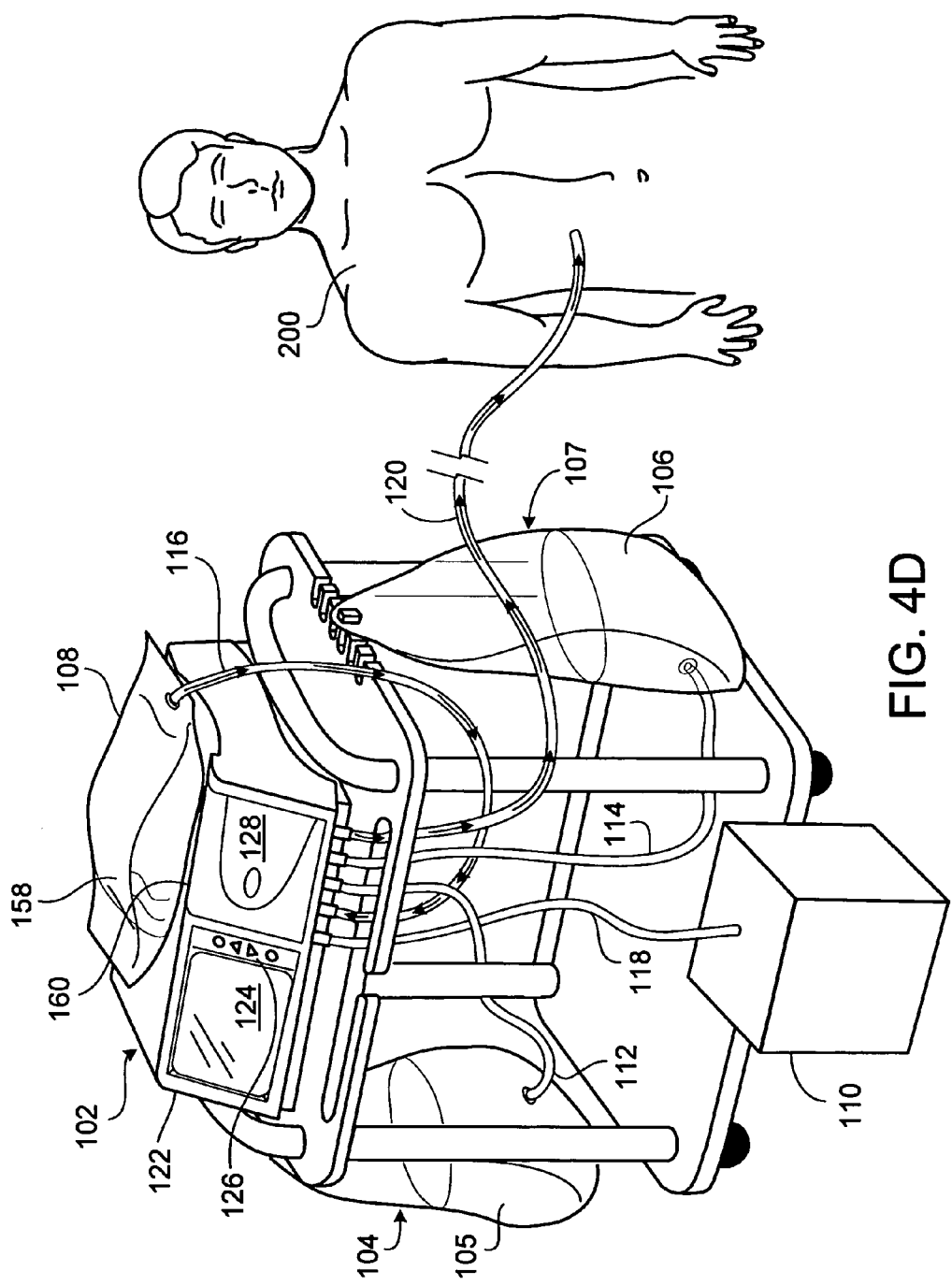

Referring to FIG. 4D, after draining a desired volume of fluid from patient 200, a fill sequence is performed to deliver custom dialysate 158 from heater bag 108 to patient 200. During the fill sequence, custom dialysate 158 is drawn from heater bag 108 into cassette 132 via heater line 116. Custom dialysate 158 is then forced out of cassette 132 and into patient 200 via patient line 120. Pumps 134 and 136 and balloon valves 146 can be operated in a manner similar to that described above with regard to delivering dialysates 105 and 107 to heater bag 108 and/or delivering fluid from patient 120 to drain container 110 in order to deliver custom dialysate 158 from heater bag 108 to patient 200. Typically about 50 ml to about 200 ml of custom dialysate 158 is delivered to the abdominal cavity of patient 200 during the fill sequence. However, depending on the size of the patient and the patient's condition, a physician can prescribe any of various volumes of dialysate to be delivered to the patient during the peritoneal dialysis treatment.

After delivering a desired amount of custom dialysate 158 to patient 200, custom dialysate 158 is allowed to dwell within the patient's abdominal cavity for a period of time. Custom dialysate 158 can, for example, remain within the patient's abdominal cavity for about 15 minutes to about 120 minutes. As a result, water and waste products (e.g., urea and creatinine) are removed from the patient's blood by a diffusion process that occurs across the peritoneum of patient 200. The concentration of dextrose in custom dialysate 158 affects that rate at which water is removed from patient 200 during this dwell sequence. Generally, the rate at which water is removed from the patient increases as the concentration of dextrose in the dialysate increases, and the rate at which water is removed from the patient decreases as the concentration of dextrose in the dialysate decreases. The desired rate with which to remove water from the patient, and thus the desired dextrose concentration in the dialysate, can depend on various factors and can vary from patient to patient. Therefore, it can be beneficial for a physician to be able to prescribe the use of dialysates having dextrose concentrations tailored to the specific needs of the patient being treated. Using custom dialysates tailored to the needs of the patient being treated can help to improve the overall comfort level of patient 200 during and after dialysis treatment. For example, based on the treatment being used, removal of an ideal amount of water from the patient may require the use of a dialysate having a specific dextrose concentration. It may, for example, be determined that using a dialysate with a higher dextrose concentration would remove too much water from the patient and using a dialysate with a lower dextrose concentration would remove too little water from the patient. Such specific dextrose concentrations may not be present in commercially available, pre-packaged dialysates. Thus, the use of custom dialysate 158, which can be formed to include dialysate concentrations tailored to the needs of specific patients, can improve certain aspects of peritoneal dialysis treatments relative to similar peritoneal dialysis treatments that use unaltered, commercially available dialysates.

In some implementations, the above-described steps of the treatment process are repeated one or more times. In certain implementations, for example, five cycles (e.g., five drain, fill, and dwell sequences) are performed. In those implementations in which multiple cycles are to be performed, dialysates 105 and 107 can be delivered to heater bag 108 during the dwell sequence to prepare for the next fill sequence.

In implementations that include multiple cycles, custom dialysate 158 can have substantially the same dextrose concentration in each cycle. This can be advantageous when a uniform rate of removal of water is desired throughout the treatment. Alternatively, as discussed below, the dextrose concentration of custom dialysate 158 can be altered from cycle to cycle.

In some implementations, a flush sequence is performed to remove air from lines 112, 114, 116, 118 (e.g., all the lines except for patient line 120) and from cassette 132 prior to performing the treatment steps discussed above. The flush sequence can be accomplished by pumping dialysate (e.g., dialysate 105 and/or dialysate 107) through lines 112, 114, 116, 118 and through cassette 132. In certain implementations, prior to treatment, a prime sequence is similarly performed to remove air from patient line 120 by pumping dialysate (e.g., dialysate 105 and/or dialysate 107) through patient line 120. In some implementations, methods of using peritoneal dialysis system 100 can also include a pause sequence, which allows the patient to disconnect from dialysis system 100 once the patient's abdominal cavity has been filled with custom dialysate 158. In such implementations, while the patient is disconnected from dialysis system 100, dialysates 105 and 107 can be transferred from supply bags 104, 106 to heater bag 108 to prepare for a subsequent fill sequence.

While certain implementations have been described, other implementations are possible.

While methods discussed above describe using sequential pumping cycles to deliver dialysates 105 and 107 to heater bag 108, in some implementations, dialysates 105 and 107 are delivered to heater bag 108 using a single pumping cycle. In such implementations, pump A can be placed in fluid communication with supply bag 104 but not supply bag 106, and pump B can be placed in fluid communication with supply bag 106 but not supply bag 104. Cassette 132 can, for example, include an additional button 152 arranged within the fluid passage 154 that connects supply bag 104 to pump B and connects supply bag 106 to pump A. Cassette deck 130 can similarly include an additional balloon valve 146 configured to depress the additional button 152 of cassette 132. During use, the additional button 152 can be depressed while operating pumps 134 and 136 such that dialysate 105 is drawn into chamber A and delivered from chamber A to heater bag 108, and dialysate 107 is drawn into chamber B and delivered from chamber B to heater bag 108 during a single pumping cycle. Pumps 134 and 136 can be operated in tandem or using an alternative pumping method. Both of these methods of operation were discussed above.

While methods described above include delivering dialysate 105 and dialysate 107 to heater bag 110 at a ratio of 1:2, dialysates 105 and 107 can be delivered to heater bag 110 in any of various other ratios, depending on the desired concentration (e.g., the prescribed concentration) of one or more solutes in the custom dialysate formed by the combination of dialysates 105 and 107 in heater bag 110.

While dialysates 105 and 107 have been described as having dextrose concentrations of 1.5 percent and 4.25 percent, respectively, dialysates 105 and 107 can have any of various other dextrose concentrations that differ from one another to allow a custom dialysate having an intermediate dextrose concentration to be prepared. Dialysates 105 and 107 can, for example, have dextrose concentrations of 1.5 percent and 2.5 percent, respectively. Alternatively, dialysates 105 and 107 can have dextrose concentrations of 2.5 percent and 4.25 percent, respectively. Any of various other combinations of dialysates can alternatively or additionally be used.

While certain implementations discussed above include two supply bags, three or more supply bags (e.g., four supply bags) can alternatively be used. In implementations including three or more supply bags, the concentrations of dextrose within each of the supply bags as well as the prescribed dextrose concentration can be input into the control unit of dialysis machine 102 via touch screen 124 prior to commencing treatment. Based on this input data, pumps 134 and 136 and balloon valves 146 can be controlled to draw dialysates from two or more of the supply bags to form the custom dialysate. Typically, in such implementations, at least two of the supply bags include diaysates with different dextrose concentrations. In some cases, more than two of the supply bags (e.g., all of the supply bags) contain dialysates with different dextrose concentrations.

In implementations involving multiple cycles (e.g., multiple drain, fill, and dwell sequences), one or more of the treatment steps can be altered in subsequent cycles. As an example, the amount of custom dialysate 158 delivered to patient 200 and/or the amount of time for which custom dialysate 158 is allowed to dwell within patient 200 can be increased or decreased.

Similarly, in implementations including multiple cycles of treatment (e.g., multiple drain, fill, and dwell sequences), the concentration of dextrose in custom dialysate 158 can be altered from cycle to cycle. The dextrose concentration of custom dialysate 158 can, for example, be profiled throughout the treatment. In some implementations, the concentration of dextrose in custom dialysate 158 is gradually decreased from cycle to cycle. For example, custom dialysate 158 can be produced to have a dextrose concentration of about 4.25 percent during the first cycle, a dextrose concentration of about 4.0 percent during a second cycle, a dextrose concentration of about 3.0 percent during a third cycle, a dextrose concentration of about 2.0 percent during a fourth cycle, and a dextrose concentration of about 1.5 percent during a fifth cycle. As a result, the amount of water withdrawn from the patient during each cycle is gradually reduced from cycle to cycle. This technique can help to rapidly relieve the patient of discomfort associated with having built up and retained excessive amounts of water since the last treatment, and can help to prevent negative side effects that can result from the removal of excessive amounts of water in the later stages of the treatment. Data regarding the desired dextrose concentration for each cycle can be input by the patient using touch screen 124 prior to treatment. Thus, the control unit of dialysis machine 102 can control pumps 134 and 136 to prepare the desired custom dialysates during each cycle.

While dialysates 105 and 107 have been described as having different dextrose concentrations, in some implementations, dialysates 105 and 107 alternatively or additionally have different concentrations of one or more other solutes, such as calcium and/or magnesium. As a result, dialysates 105 and 107 can be combined to form a custom dialysate having a desired concentration of calcium and/or magnesium that is intermediate to the concentrations of calcium and/or magnesium found in dialysates 105 and 107. It may, for example, be beneficial to use a dialysate having a concentration of calcium and/or magnesium that differs from the concentrations of calcium and/or magnesium typically found in commercially available, pre-packaged dialysates. The concentration of calcium and/or magnesium in the custom dialysate can, for example, be tailored to the specific condition of the patient to be treated. In some implementations, first dialysate 105 has a calcium concentration of about 2.5 mEq/L and second dialysate 107 has a calcium concentration of about 2.5 mEq/L. In certain implementations, first dialysate 105 has a magnesium concentration of about 0.5 mEq/L and second dialysate 107 has a magnesium concentration of about 1.5 mEq/L.

In implementations in which multiple treatment cycles are performed, as an alternative to or in addition to changing the concentration of dextrose in the custom dialysate used from cycle to cycle, the concentration of calcium and/or magnesium in the custom dialysate can be changed from cycle to cycle. The concentration of calcium and/or magnesium in the custom dialysates can, for example, be gradually decreased from cycle to cycle.

While the methods described above include controlling pumps 134 and 136 to regulate the amount of dialysates 105 and 107 transferred to heater bag 108, other techniques can alternatively or additionally be used to ensure that desired amounts of dialysates 105 and 107 are delivered to heater bag 108 to form the custom dialysate. For example, the weight of fluid delivered to heater bag 108 can be measured to determine the amounts of dialysates 105 and 107 therein. In certain implementations, for example, heater tray 160 is equipped with a weight measuring unit (e.g., a measuring scale). In such implementations, first dialysate 105 can be delivered to heater bag 108 until a desired weight, which correlates to a desired volume, of first dialysate 105 resides within heater bag 108. Subsequently, second dialysate 107 is delivered to heater bag 108 until a desired weight, which correlates to a desired volume, of second dialysate 107 resides within heater bag 108. Alternatively, second dialysate 107 can be delivered to heater bag prior to delivering first dialysate 105. In those implementations that rely on the weight of the dialysate delivered to heater bag 108 to deliver desired amount of dialysates to heater bag 108, the weight measuring unit can be in communication with the control unit of dialysis machine 102. As a result, the control unit can control pumps 134 and 136 to deliver the desired amounts of dialysate based on feedback from the weight measuring unit during use.

While the methods described above include mixing dialysates together to form a custom dialysate having an intermediary concentration of one or more solutes, other types of substances can alternatively or additionally be mixed together to form the custom dialysate. In some implementations, for example, a highly concentrated dialysis solution (e.g., dialysate concentrate) is combined with a liquid (e.g., reverse osmosis water and/or sterile saline) to form a custom dialysate having a desired concentration of one or more solutes, such as dextrose, calcium, and/or magnesium. The dialysate concentrate can have a dextrose concentration of about 10 percent to about 30 percent, a calcium concentration of about 5.9 mEq/L to about 70 mEq/L, and/or a magnesium concentration of about 1.2 mEq/L to about 30 mEq/L. The diaysate concentrate and liquid can be combined at a ratio of about 1:4 to about 1:20 to form a custom dialysate for use in peritoneal dialysis treatments.

While certain methods above describe combining dialysate 105 with dialysate 107 to form custom dialysate 158, other techniques can be used. In certain implementations, for example, a third substance (e.g., a drug and/or a nutritional supplement) is introduced along with dialysates 105 and 107 to form the custom dialysate. The third substance can, for example, be a substance, such as a vitamin, of which the patient has insufficient levels. In such implementations, the custom dialysate can be used to replenish the patients levels of the substance in addition to removing excess water and waste from the patient. In certain implementations, a substance (e.g., a drug and/or a nutritional supplement) is combined with a single dialysate (e.g., a single commercially available, pre-packaged dialysate) to form the custom dialysate. The substance can, for example, be added to the dialysate where levels of the substance exceeding those found in the dialysate would help to improve peritoneal dialysis treatments. For example, a vitamin can be added to the dialysate when the patient has insufficient levels of that vitamin in his/her body. Alternatively or additionally, a nutritional supplement can be used where the patient is malnourished. In such implementations, the concentration of the substance (e.g., the drug and/or nutritional supplement) to be produced in the custom dialysate can be prescribed by a physician and input into dialysis machine 102 by the patient using touch screen 124.

While the methods described above include placing heater bag 108 on heater tray 160 to heat custom dialysate 158, other heating methods can alternatively or additionally be used. In some implementations, for example, dialysates 105 and 107 are passed through a flash heater prior to being delivered to the patient. In such implementations, dialysates 105 and 107 can be passed through the flash heater prior to or subsequent to being combined to form the custom dialysate. In some implementations, for example, the flash heater is provided on a fluid line extending from peritoneal dialysis machine 102 to the patient. In such embodiments, the dialysates can be delivered to a mixing bag to form a custom dialysate therein, and then, from the mixing bag, the custom dialysate can be passed through the flash heater on its way to the patient. Alternatively, in some implementations, the dialysates are transferred directly from the supply bags to the patient. In such implementations, the dialysates can be both mixed together and heated within a line connecting the supply bags to the patient.

While system 100 of the methods describes above includes drain container 110, any of various other devices and/or techniques can be used to dispose of the used dialysate. In certain implementations, systems can be operated without a drain container. In such implementations, drain line 118 can be connected to a drain tub to provide for disposal of the used dialysate.

Other implementations are in the claims.

What is claimed is:

1. A method of performing peritoneal dialysis, the method comprising:
    receiving input data regarding a prescribed dextrose concentration and a dextrose concentration of each of a plurality of different commercially available, pre-packaged dialysates, wherein the dextrose concentrations of the pre-packaged dialysates differ from one another;
    disposing a first dialysate having a first concentration of dextrose in an abdominal cavity of a patient for a first period of time, and then removing the first dialysate from the abdominal cavity of the patient after the first period of time;
    after removing the first dialysate from the abdominal cavity of the patient, disposing a second dialysate having a second concentration of dextrose in the abdominal cavity of the patient for a second period of time, and then removing the second dialysate from the abdominal cavity of the patient after the second period of time, the second concentration of dextrose being lower than the first concentration of dextrose; and
    after removing the second dialysate from the abdominal cavity of the patient, disposing a third dialysate having a third concentration of dextrose in the abdominal cavity of the patient for a third period of time, and then removing the third dialysate from the abdominal cavity of the patient after the third period of time, the third concentration of dextrose being lower than the second concentration of dextrose,
    wherein the first, second, and third dextrose concentrations are determined based on the input data, and wherein disposing the first, second, and third dialysates in the abdominal cavity comprises delivering at least a portion of at least one of the pre-packaged dialysates to the abdominal cavity, and at least one of the first, second, and third dialysates is a mixture of the plurality of pre-packaged dialysates.

2. The method of claim 1, further comprising combining the plurality of pre-packaged dialysates in a mixing container to form the first dialysate.

3. The method of claim 2, further comprising combining the plurality of pre-packaged dialysates in the mixing container to form the second dialysate and the third dialysate.

4. The method of claim 1, further comprising delivering pre-packaged dialysate to a mixing container from a first supply bag.

5. The method of claim 4, wherein delivering the pre-packaged dialysate from the first supply bag to the mixing container comprises pumping the pre-packaged dialysate through a line that fluidly connects the first supply bag to the mixing container.

6. The method of claim 4, further comprising delivering pre-packaged dialysate to the mixing container from a second supply bag.

7. The method of claim 6, wherein delivering the pre-packaged dialysate from the second supply bag to the mixing container comprises pumping the pre-packaged dialysate through a line that fluidly connects the second supply bag to the mixing container.

8. The method of claim 2, wherein the mixing container comprises a heater bag.

9. The method of claim 8, further comprising heating the heater bag such that the first dialysate, when disposed within the heater bag, is warmed.

10. The method of claim 2, wherein the mixing container comprises a fluid line.

11. The method of claim 10, wherein the fluid line is in fluid communication with the abdominal cavity of the patient.

12. The method of claim 10, wherein the first dialysate is heated within the fluid line prior to being disposed within the abdominal cavity of the patient.

13. The method of claim 12, wherein the fluid line comprises a flash heater.

14. The method of claim 2, wherein predetermined volumes of each of the plurality of pre-packaged dialysates are delivered to the mixing container to form the first, second, and third dialysates.

15. The method of claim 14, wherein a pump is actuated in a manner to deliver the predetermined volumes of the plurality of pre-packaged dialysates to the mixing container.

16. The method of claim 15, wherein the pump is in communication with a control unit adapted to control a displacement of the pump, a volume of the plurality of pre-packaged dialysates delivered by the pump being proportional to the displacement of the pump.

17. The method of claim 14, further comprising determining the predetermined volumes of the plurality of pre-packaged dialysates based on desired dextrose concentrations in the first, second, and third dialysates.

18. The method of claim 14, wherein respective volumes of the plurality of pre-packaged dialysates delivered to the mixing container to form the first dialysate differ from respective volumes of the plurality of pre-packaged dialysates delivered to the mixing container to the form the second dialysate, and respective volumes of the plurality of pre-packaged dialysates delivered to the mixing container to form the second dialysate differ from respective volumes of the plurality of pre-packaged dialysates delivered to the mixing container to form the third dialysate.

19. The method of claim 1, wherein the first concentration of dextrose is about 4.25 percent, the second concentration of dextrose is about 4.0 percent, and the third concentration of dextrose is about 3.0 percent.

20. The method of claim 1, wherein the first concentration of dextrose is about 3.0 percent, the second concentration of dextrose is about 2.0 percent, and the third concentration of dextrose is about 1.5 percent.

21. The method of claim 1, wherein the first, second, and third dialysates have first, second, and third concentrations, respectively, of a solute, the first, second, and third concentrations of the solute differing from one another.

22. The method of claim 21, wherein the solute comprises magnesium.

23. The method of claim 1, further comprising disposing an additional substance in the abdominal cavity of the patient.

24. A method of performing peritoneal dialysis treatment, the method comprising:
combining a dialysate concentrate having a dextrose concentration of ten percent to 30 percent, a calcium concentration of about 5.9 mEq/L to about 70 mEq/L, and a magnesium concentration of about 1.2 mEq/L to about 30 mEq/L with a diluent to form a first dialysate, wherein the diluent is reverse osmosis water or saline;
disposing the first dialysate in an abdominal cavity of a patient for a first period of time; and
removing the first dialysate from the abdominal cavity of the patient after the first period of time.

25. The method of claim 24, wherein the diluent comprises reverse osmosis water.

26. The method of claim 24, further comprising:
combining the dialysate concentrate with the diluent to form a second dialysate, the second dialysate having a dextrose concentration that differs from a dextrose concentration of the first dialysate;
disposing the second dialysate in the abdominal cavity of the patient for a second period of time; and
removing the second dialysate from the abdominal cavity of the patient after the second period of time.

27. The method of claim 26, wherein respective volumes of the dialysate concentrate and diluent combined to form the second dialysate differ from respective volumes of the dialysate concentrate and diluent combined to form the first dialysate.

28. The method of claim 26, further comprising:
combining the dialysate concentrate with the diluent to form a third dialysate, the third dialysate having a dextrose concentration that differs from dextrose concentrations of the first and second dialysates;
disposing the third dialysate in the abdominal cavity of the patient for a third period of time; and
removing the third dialysate from the abdominal cavity of the patient after the third period of time.

29. The method of claim 24, further comprising disposing another substance in the abdominal cavity of the patient.

30. A peritoneal dialysis system, comprising:
a first container containing a dialysate concentrate having a dextrose concentration of ten percent to 30 percent, a calcium concentration of about 5.9 mEq/L to about 70 mEq/L, and a magnesium concentration of about 1.2 mEq/L to about 30 mEq/L;
a second container containing a diluent, wherein the diluent is reverse osmosis water or saline;
a mixing container in fluid communication with the first and second containers; and
a pump configured to pump metered amounts of the dialysate concentrate and the diluent to the mixing container to form a dialysate.

31. The peritoneal dialysis system of claim 30, further comprising a control unit in communication with the pump, the control unit adapted to control the amounts of the dialysate concentrate and diluent that are pumped to the mixing container.

32. The peritoneal dialysis system of claim 31, wherein the control unit is adapted to control the amounts of the dialysate concentrate and diluent that are pumped to the mixing container based on a desired concentration of a solute in a dialysate to be formed in the mixing container upon combining the dialysate concentrate and diluent.

33. The peritoneal dialysis system of claim 32, wherein the control unit is adapted to receive input data and to control amounts of the dialysate concentrate and diluent that are pumped to the mixing container based on the input data.

34. The peritoneal dialysis system of claim 33, wherein the input data comprises a dialysate prescription.

35. The peritoneal dialysis system of claim 32, wherein the solute comprises dextrose.

36. The peritoneal dialysis system of claim 32, wherein the solute comprises calcium.

37. The peritoneal dialysis system of claim 32, wherein the solute comprises magnesium.

38. The peritoneal dialysis system of claim 30, wherein the mixing container comprises a heater bag.

39. The peritoneal dialysis system of claim 38, further comprising a heating element adapted to heat dialysate within the heater bag.

40. The peritoneal dialysis system of claim 30, wherein the diluent comprises reverse osmosis water.

41. The method of claim 1, wherein the commercially available, pre-packaged dialysates are supplied in bags.

* * * * *